(12) United States Patent
Amir et al.

US007677103B2

(10) Patent No.: US 7,677,103 B2
(45) Date of Patent: Mar. 16, 2010

(54) SYSTEMS AND METHODS FOR NON-DESTRUCTIVE TESTING OF TUBULAR SYSTEMS

(75) Inventors: Noam Amir, Ness Ziona (IL); Tal Pechter, Ramat Hasharon (IL)

(73) Assignee: Acousticeye Ltd., Ramat Hasharon (IL)

( * ) Notice: Subject to any disclaimer, the term of this patent is extended or adjusted under 35 U.S.C. 154(b) by 474 days.

(21) Appl. No.: 11/495,642

(22) Filed: Jul. 31, 2006

(65) Prior Publication Data

US 2007/0034012 A1 Feb. 15, 2007

Related U.S. Application Data

(60) Provisional application No. 60/703,450, filed on Jul. 29, 2005.

(51) Int. Cl.
*G01N 29/04* (2006.01)
*G01N 29/30* (2006.01)

(52) U.S. Cl. .............................. 73/627; 73/1.82; 73/602; 73/644; 381/59

(58) Field of Classification Search .................... 73/598, 73/1.16, 1.73, 290 V, 53.04, 602, 861, 1.82, 73/627, 644, 23.29; 367/99, 908
See application file for complete search history.

(56) References Cited

U.S. PATENT DOCUMENTS

| 4,483,195 | A | * | 11/1984 | Brown et al. ................... 73/702 |
| 5,307,140 | A | * | 4/1994 | Lewis ......................... 356/73.1 |
| 5,450,753 | A | * | 9/1995 | Maynor et al. ................. 73/644 |
| 5,822,274 | A | * | 10/1998 | Haynie et al. .................. 367/99 |
| 5,902,252 | A | * | 5/1999 | Hohlfeld et al. .............. 600/559 |
| 6,097,478 | A | * | 8/2000 | Berthold et al. ............. 356/35.5 |
| 6,330,831 | B1 | * | 12/2001 | Lynnworth et al. ........ 73/861.28 |
| 6,354,734 | B1 | * | 3/2002 | Curran et al. ................ 374/148 |
| 6,646,451 | B2 | * | 11/2003 | Lanan ......................... 324/642 |
| 7,017,415 | B2 | * | 3/2006 | Harrold et al. ................. 73/702 |
| 2008/0208505 | A1 | * | 8/2008 | Amir et al. ................... 702/103 |

* cited by examiner

*Primary Examiner*—J M Saint Surin
(74) *Attorney, Agent, or Firm*—Mark M. Friedman

(57) ABSTRACT

Method and systems for non-destructive testing of a gas or liquid filled object at atmospheric pressure or high pressure. The method includes steps of: providing an acoustic pulse reflectometry (APR) system having a wideband transmitter, a pressure sensor and a short mixed wave tube, performing at least one calibration to obtain at least one calibration parameter; attaching the object to the APR system and performing a measurement to obtain an object test result and processing the object test result and the at least one calibration parameter to obtain an object impulse response that reflects a status of the object.

20 Claims, 12 Drawing Sheets

SYSTEMS AND METHODS FOR NON-DESTRUCTIVE TESTING OF TUBULAR SYSTEMS

CROSS REFERENCE TO EXISTING APPLICATIONS

This application claims priority from U.S. Provisional Patent Application No. 60/703,450 filed 29 Jul. 2005.

FIELD OF THE INVENTION

The present invention relates generally to non-destructive testing (NDT) systems and methods and more particularly to acoustic pulse reflectometry (APR) systems and methods used in tubular objects.

BACKGROUND OF THE INVENTION

Acoustic pulse reflectometry is the generic name given to a family of techniques used to measure the acoustic response of a given system. Its application to systems consisting of volumes of air bound by rigid surfaces is known. The term "APR" is derived from the fact that an excitation pulse (or "impulse") is applied to the system, and the reflections created inside the system are then measured. The pulse need not be "real", but may be in the form of pseudo-noise or frequency sweeps, see below. Various algorithms are applied to this acoustic response, in order to gain information regarding the system being examined.

Ideally, APR should enable extraction of the theoretical impulse response of the system being measured. In practice this is impossible, since an ideal pulse has an infinite bandwidth (BW), and therefore cannot be created under laboratory conditions. Normally a very short electrical pulse is applied to a transducer, producing an acoustic pulse of short duration, and as large a BW as possible. The transducer is coupled through a tube to the system or "object" being measured, with a microphone mounted in the tube wall. The microphone measures both the excitation pulse and the reflections from the object.

FIG. 1 shows a typical setup of a prior art APR system. A transducer emits an acoustic wave that propagates down two tubes, a left one with length L1 and a right one with length L2. The lengths L1 and L2 change according to the object being measured, and are typically between 3 and 6 meters. The wave is recorded as it propagates over the microphone. It then arrives at an object, creating reflections that propagate back down the tubes. These reflections are also recorded as they pass over the microphone. If the two tubes are sufficiently long, the right and left propagating waves do not overlap, and are recorded separately. From a purely experimental point of view, several technical problems are encountered in this type of setup:

1. The acoustic pulse typically has high amplitude, but is very short in duration. This results in a pulse having rather low energy content. This makes it difficult to obtain a high signal to noise ratio (SNR) in the reflections measured from the object.
2. The excitation pulse and the reflections from the object have finite duration, which can cause them to overlap at the microphone. This can make them very difficult to separate.
3. Reflections from the object eventually travel down to the transducer itself, reflect off it, and return to be measured once again by the microphone. These secondary reflections can once more interfere with measurements of the response of the object.

Once the acoustic response has been measured, several types of analyses can be applied. In most cases, the first step is deconvolution of the reflected pulse and the excitation pulse [see e.g. N. Amir, G. Rosenhouse, U. Shimony, Acustica, Vol. 81, pages 450-462 and 463-474, 1995 (hereinafter "Amir1")]. Deconvolution must be carried out, normally through division in the frequency domain or Singular Value Decomposition (SVD), because the excitation pulse rarely has a flat spectrum. Further analysis depends on the purpose of the measurements and the geometrical nature of the object being studied. Two typical problems arise according to two different applications:

Bore reconstruction: in this type of application, the system being examined is considered to be one-dimensional, i.e. it is much longer than its cross section, in the manner of a long tube, possibly having a varying cross section. Current methods assume that no transverse modes are excited in the tube, a fact that limits the usable bandwidth. This is somewhat in conflict with the objective of attaining an excitation pulse having the largest possible bandwidth, and some compromise must be reached. Once the impulse response of this kind of system is measured, various algorithms can be used to reconstruct the cross section of the tube—this is termed "bore reconstruction". The most common algorithms are variants of the "layer-peeling algorithm" originally proposed by Ware and Aki in J. Acoust. Soc. Am., Vol. 45, pages 911-921, 1969. Other similar models include Amir1 above. The axial resolution of the reconstruction is determined by the bandwidth of the excitation pulse, whereas the accuracy in calculating the cross section is determined by the deconvolution process and the SNR. It is important to stress that as long as the cross section preserves the condition that no transverse modes are excited, it can be reconstructed with no other a-priori information.

Quality Assurance: in this type of application we wish to determine the conformity between an accurately measured prototype and a test object, such as components coming off a manufacturing line, or tubing in an aircraft being checked during routine maintenance. In such a case, acoustic measurements can be carried out on the prototype, with no particular constraints on its internal geometry. The acoustic signature of the prototype can then be compared to measurements taken from manufactured parts, in order to detect faults (leaks, internal deformations, blocked passageways etc.). This can be applied to various types of tubing, manifolds, cooling passageways in cast parts, etc. In the simplest case, any deviations from the prototypical measurements that fall out of predetermined limits can flag a fault. In the more general case, the measurements can be interpreted by automated algorithms, in order to determine the exact nature and location of faults.

Various APR systems and methods that attempted to solve some of the problems mentioned above are known and described for example in Japanese patents JP 7-55949, JP 7-71700, JP 7-198527, JP 7-198528, JP 11-125623 and patent applications (JP 2003-207329)

JP 7-55949 applies APR to find joints in a pipe. Both transmission (TX) and reception (RX) elements are at one end of pipe. Joints in the pipe create reflections that arrive earlier than the reflection from end of pipe. Peaks in the reflected signal are interpreted as joints, therefore this patent does not mention deconvolution of the reflections with the excitation signal. This would probably result in major inaccuracies.

JP 2003-207329 applies APR to find joints and elbows in pipes based on reflection travel time and waveform. The TX is placed at one end of the pipe, with RX in a side pipe not far from TX. The joints are far-enough apart so that reflections do not overlap, and there is no calibration of the TX pulse shape or loudspeaker impulse response, no deconvolution and no leak detection.

JP 7-198527 and JP 7-198528 apply APR to find gas leaks in a supply pipe to a household gas system. TX and RX are near each other at the inlet port of the gas meter. The method compares the "normal" (nominal or calibrated) response of the complete pipe system to measurements taken when the system is being tested. JP 11-125623 discloses an APR system with TX and RX at the same end of a pipe. The state objective of this patent is to detect (unspecified) types of joints or "troubles". The method uses either frequency sweep or pseudo-noise measurements. The frequency response of the reflections is compared to a library of previous measurements of the joints that system intends to detect. There is no calibration of the loudspeaker impulse, nor mention of deconvolution. The system can detect only objects that have been measured previously and stored in memory.

A common problem in APR systems is the presence of background noise, especially when such measurements are carried out in the field, as opposed to ideal laboratory conditions. This problem is discussed in most academic publications on the subject. Several methods have been proposed in the literature to improve the Signal to Noise Ratio (SNR). One method is to carry out tens or hundreds of measurements successively and average them [Amir1]. Incoherent background noise is reduced considerably this way, though this method prolongs the measurement process to an extent that is unacceptable in certain setups. Other methods involve the use of pseudo-noise signals [Forbes et al. Acta Acustica Vol. 89, pages 743-753, 2003] or frequency sweeps, from which the impulse response can be extracted mathematically. Both methods require much shorter measurement times and are therefore implemented in the proposed system. Thus, it should be understood that an APR system does not necessarily use real pulses but can also use pseudo noise or frequency sweeps. Hereinafter, "APR" is meant to include all types of pulses.

Presently, a major drawback in implementing APR is the presence of long tubes (L1 and L2 in FIG. 1) on either side of the measurement microphone. These cause the instrument to be extremely bulky, even when they are coiled. They also introduce a large degree of attenuation, which limits the accuracy and the range of the instrument. These tubes are the simplest means to prevent the excitation pulse and the reflections from overlapping at the microphone, by creating time delays that prevent this overlap. On the other hand, propagation through these tubes causes attenuation of high frequencies, thereby reducing the bandwidth of the pulse impinging on the object, and reducing the effective range of the equipment. A method to reduce the length of the tubing on only one side of the microphone has been published recently [A. Li, D. B. Sharp and B. J. Forbes, Proc. of the International Symposium on Musical Acoustics, Perugia, Italy, 8-14 Sep. 2001; pp. 391-394].

Separation of overlapping pulses in APR using short tubes on both sides of the microphone has been attempted before, without success [Amir1]. The method requires:
1. Prior measurement of two values:
   a. The excitation pulse emitted by the loudspeaker, $P_1$
   b. The acoustic impulse response of the excitation loudspeaker to an impinging pulse $H_i$.
2. Applying an algorithm to separate the impulse response of the object from the overlapping measurements. This is based on applying the following formula:

$$H_s = \frac{Z_i - 1}{Z_i H_i + 1} \quad (1)$$

where:

| | |
|---|---|
| $H_s$ | The impulse response of the object (transformed to the freq. domain) This is the value seeked. |
| $Z_i$ | The impulse response of the entire system, including the overlapping reflections. Mathematically $Z_i = P_M/P_1$, where $P_M$ is the raw measurement of the system, and $P_1$ is the measured excitation pulse. This is a measured value |
| $H_i$ | The impulse response of loudspeaker, obtained from the calibration process (transformed to the freq. domain). This is a value that must be obtained through calibration measurements. |

Errors in accurately deriving $Z_i$ and $H_i$ and various numerical sensitivities in applying the above formula caused this method to give poor results.

Once accurate measurement data is obtained, it is important to perform correct interpretation of this data in order to detect faults, and find their type and location if these are present. Existing methods found in academic literature or patents are based on several techniques. The first is peak detection. Strong reflections arriving before the reflections expected from the end of the pipe indicate discontinuities, though they provide very little information as to their character. In complicated systems where there are valid discontinuities such as changes in cross sections, finding the peaks related only to faults can be difficult and unreliable. A slightly more advanced method is based on comparison to previous measurements of faults. This method is also simplistic, since different sized leaks will have different acoustic patterns, and it may not be feasible to store a large number of such patterns. Furthermore, acoustic wave propagation properties change with temperature and moisture, so that library measurements may not fit well with field measurements taken under varied conditions.

A more general method for fault detection is to apply the general bore reconstruction method [see e.g. V. Chilekawa, D. B. Sharp, T. J. W. Hill, Proc. of the Stockholm Music Acoustics Conference, Stockholm, Sweden, Aug. 6-9, 2003 (hereinafter "Chilekawa"); D. B. Sharp and D. M. Campbell, Acustica 83, 560-566, 1997]. This method is most suited to the detection of obstruction and blockages, since it breaks down in the case of leaks. This method is also sensitive to low frequency noise, when present. Bore reconstruction has been applied to detection of leaks, by taking advantage of the fact that it breaks down in their presence (Chilekawa). As shown in the latter reference, this method is most useful if separate measurements can be taken from either side of the tube, which is rarely feasible. Otherwise, application of the bore reconstruction algorithm gives a false indication of a steadily increasing flare, which can be interpreted as a leak if a priori knowledge indicates that such a flare is not in fact present. Automated detection of such a false flare is not straightforward [Chilekawa], especially when it is located near other discontinuities in the tube.

In summary, to be useful, equipment based on APR should have the following features:
1. Short measurement time
2. High robustness to noise 3. Low bulk
4. Easy and accurate calibration methods
5. Robust and accurate fault detection methods, that do not require previous measurements of each type of fault No prior art APR method and system provide all of these features. It is thus desirable to have an APR technology that can provide satisfactory answers to the problems outlined above.

SUMMARY OF THE INVENTION

The present invention provides an elegant solution to the long standing problem of signal overlap, described in the Background. Previous solutions are improved on by the use of a combination of signal processing techniques and a separation algorithm with reduced numerical sensitivity. The present solution, embodied in both systems and methods, uses an APR system with a mixed wave tube and unique calibrations.

According to the present invention there is provided a method for non-destructive testing of an object, including steps of providing an APR system having a wideband transmitter, a pressure sensor and a mixed tube with length 2 L, performing a calibration to obtain two calibration parameters, an exact acoustic excitation pulse form $P_1$ and a loudspeaker acoustic impulse response $H_i$, attaching the object to the APR system and performing a measurement to obtain an object test result $P_M^o$, and using $P_1$, $H_i$ and $P_M^o$ to obtain an object impulse response $H_s$ whereby the object impulse response reflects a status of the object.

In some embodiments of the method, the obtaining of $P_1$ includes performing a measurement selected from the group consisting of a measurement that measures $P_1$ while a semi-infinite tube serves as the object and a measurement on an object in which any faults are far enough from the connection to the mixed wave tube so that $P_1$ can be extracted from this measurement According to the present invention there is provided an APR system for non-destructive testing of a pressurized test object, including a wide band signal transmitter for providing source acoustic pulses, a mixed wave tube for serving as conduit for the source pulses between the transmitter and object, a pressure sensor equidistantly spaced between two opposite ends of the mixed tube and used for sensing impulse responses from the test and calibration objects and means for pressurizing the mixed wave tube, calibration and test objects, thereby enabling non-destructive testing of a pressurized object.

According to the present invention there is provided an APR system for non-destructive testing of a test object filled with liquid, including a wide band signal transmitter for providing source acoustic pulses, a mixed wave tube for serving as conduit for the source pulses between the transmitter and object, a pressure sensor equidistantly spaced between two opposite ends of the mixed tube and used for sensing impulse responses from the test and calibration objects and means for introducing and removing a liquid into or from the mixed wave tube, calibration and test objects, thereby enabling non-destructive testing of a liquid filled object.

According to the present invention there is provided a method for calibrating an APR system that can be used to non-destructively measure an object, the method comprising steps of measuring the acoustic excitation pulse form $P_1$ as emitted by the loudspeaker and using the measured $P_1$ to determine a loudspeaker acoustic impulse response $H_i$, whereby both $P_1$ and $H_i$ can be further used in determining non-destructively a status of a measured object.

In some embodiments of the method for calibrating an APR system according to the present invention, the step of measuring $P_1$ includes performing a measurement selected from the group consisting of a measurement that measures $P_1$ while a semi-infinite tube serves as the object and a measurement on an object in which any faults are far enough from the mixed tube so that $P_1$ can be extracted from the measurement In some embodiments of the method for calibrating an APR system according to the present invention, the using the measured $P_1$ to obtain $H_i$ includes replacing the semi-infinite tube with a rigid plug, carrying out a measurement with the rigid plug to obtain a value $P_M^P$ and extracting $H_i$ directly from $P_M^P$ by a theoretical calculation that also uses the measured $P_1$.

In other embodiments of the method for calibrating an APR system according to the present invention, the using the measured $P_1$ to obtain $H_i$ includes replacing the semi-infinite tube with a rigid plug, carrying out a first measurement $P_M^P$ with the rigid plug and replacing the plug with a second object with a length L, the second object having a distal plugged end, carrying out a second measurement to obtain an added measurement $P_M^{P2}$ and calculating $H_i$ using $P_M^P$, $P_M^{P2}$ and $P_1$.

BRIEF DESCRIPTION OF THE DRAWINGS

The invention is herein described, by way of example only, with reference to the accompanying drawings, wherein.

DESCRIPTION OF THE PREFERRED EMBODIMENTS

The present invention relates to APR systems used for non-destructive testing of tubular objects held at atmospheric pressure or high pressure or filled with an un-pressurized/pressurized liquid. In this description, "tubular system" and "tubular object" (or simply "object") are used interchangeably. Examples of tubular systems are fuel and hydraulic pipes in airplanes, ships, or cars; air or gas filled tubular systems such as exhaust pipes, musical instruments, cooling systems such as heat exchangers, cooling systems or condensers in power plants; and drilled or cast cooling passages in casings and blocks.

As mentioned (Amir1), short tubes used in APR systems create a situation in which the successive reflections from the object and the loudspeaker overlap at the microphone. As discussed above, this creates a major difficulty in interpreting the measurements. A key inventive aspect of the invention includes combining the use of short tubes (termed hereinafter "mixed wave tubes") with a measurement methodology that yields superior measurement results over prior art. Another key inventive aspect lies in the methods used to interpret the measurements in order to discover faults in the measured pipe system. Several alternative methods are applied to analysis of the signals depending on the a-priori information regarding the system being examined.

Figure 2:
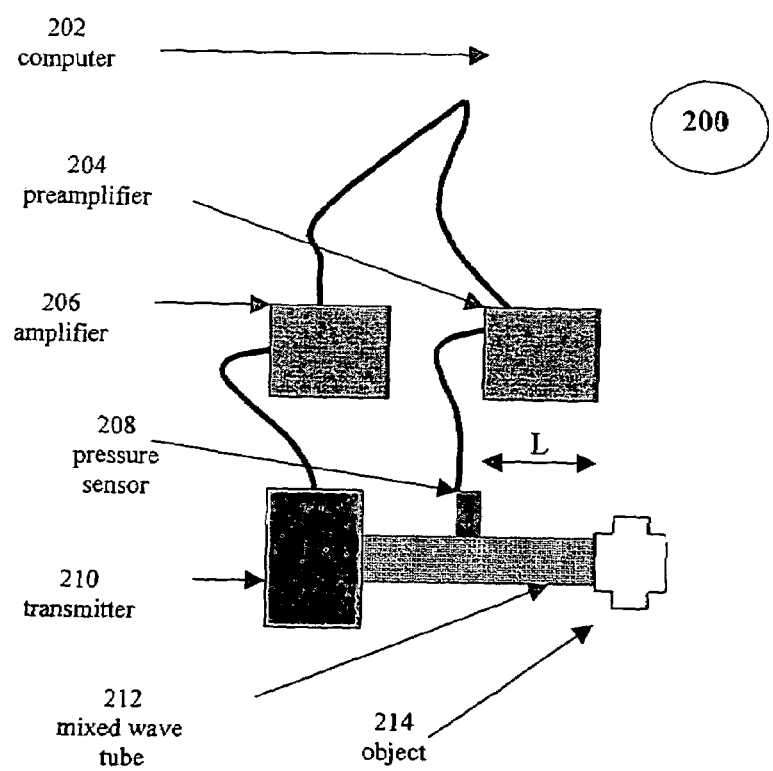
FIG. 2 shows schematically a preferred embodiment of an acoustic pulse reflectometer (APR) according to the present invention.

FIG. 2 shows schematically a preferred embodiment of an APR system 200 according to the present invention. APR system 200 includes a computer 202 with a data acquisition card (DAQ), a pre-amplifier 204 with an optional data conditioner component (not shown), an amplifier 206 with an optional data conditioner component (not shown), a pressure sensor (also referred to in the art as "microphone" or "receiver") 208, a wide band signal transmitter 210 (also referred to in the art as "transducer" or "loudspeaker") and a mixed wave tube 212. The term "mixed wave tube" as used herein means a tube in which signals propagating therein rightward and leftward overlap at sensor 208. All successfully implemented prior art APR methods employed tubes long enough so that right and left propagating signals did not overlap at the sensor. Note that there is no absolute length that determines the tubes a-priori as being "mixed", since this length depends on the time span of the signals generated in the system. Thus, in some systems, the signals might overlap even if the tubes are as long as 5 meters, while in others they may overlap for much shorter tubes. In the APR system of the present invention, mixed wave tubes are typically of 40 cm long, in the interest of keeping the system portable. However, this particular length should not be read as a limitation, as other lengths may equally suit the purposes set forth herein.

Figure 1:
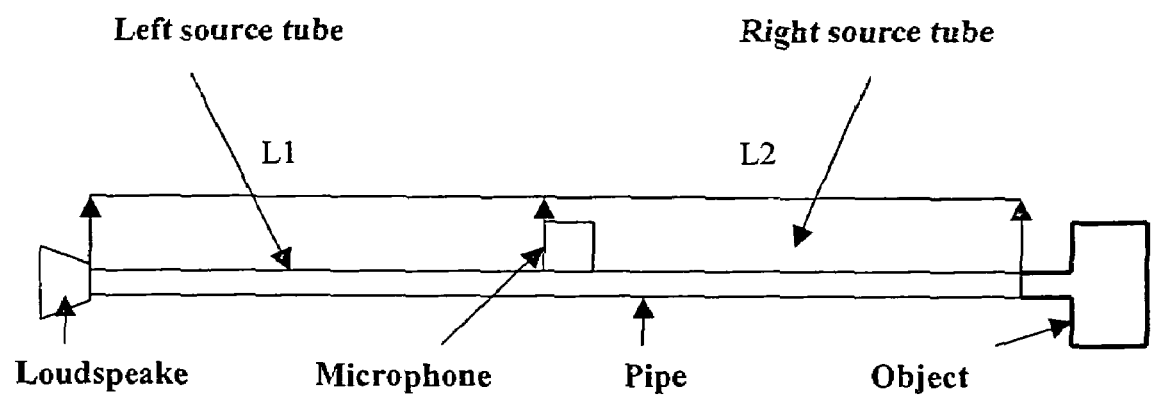
FIG. 1 shows a common APR system.

The mixed tube is connected to an "object" 214 being examined. Note that components 202-206 normally exist in every APR system, including that of FIG. 1, where they are not shown. Computer 202 creates an excitation signal which is output through the data acquisition card to amplifier 206, which passes it to transmitter 210. Sensor 208 measures the acoustic waves propagating in the tubes and passes the electrical signal for initial amplification in component 204. The amplified electrical signal is then recorded in the computer 202 after sampling by the data acquisition card.

Figure 9A:
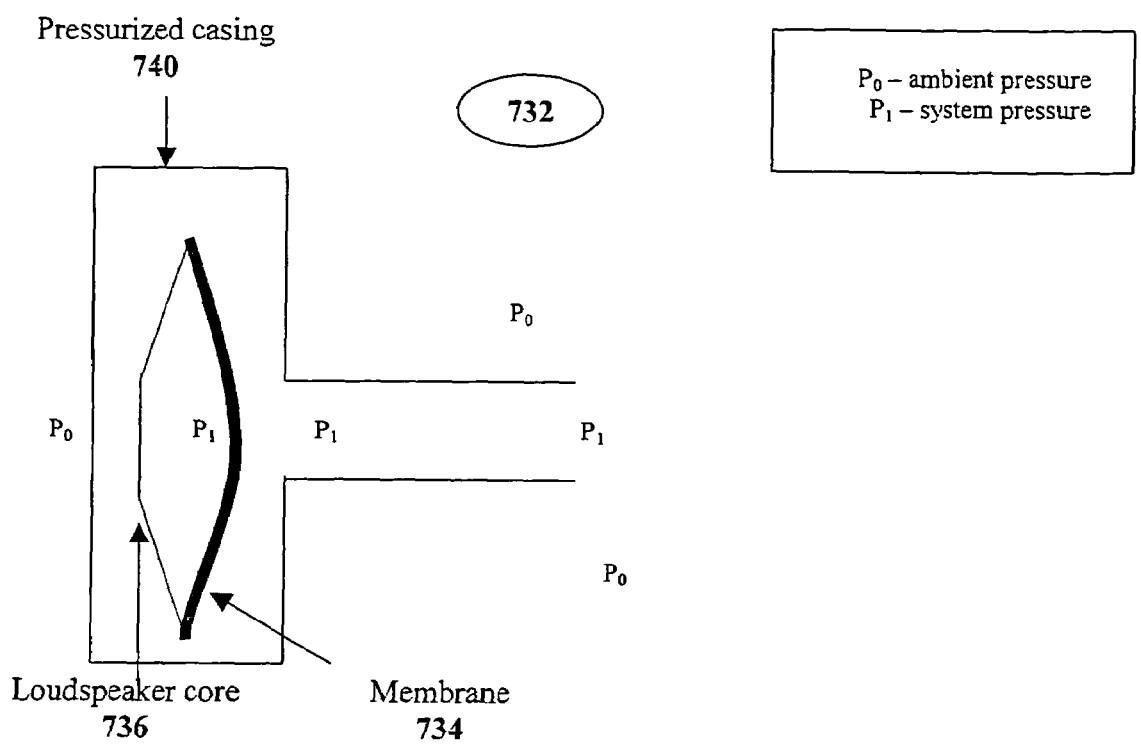
FIG. 9a shows preferred embodiments of transmitters for a pressurized APR system: (a) a standard transmitter with a pressurized casing, and (b) a sealed piezoelectric transmitter.

Inventively and in contrast with prior art, system 200 can have tubes that are filled with a liquid such as water, hydraulic oil, fuel, etc, at ambient or high pressure, or air or another gas at high pressure. In pressurized uses, transmitter 210 may be included in a high pressure casing (see below, FIG. 9a). The general methodology described hereinbelow applies to both air, gas and liquid filled objects, pressurized or un-pressurized.

Figure 3:
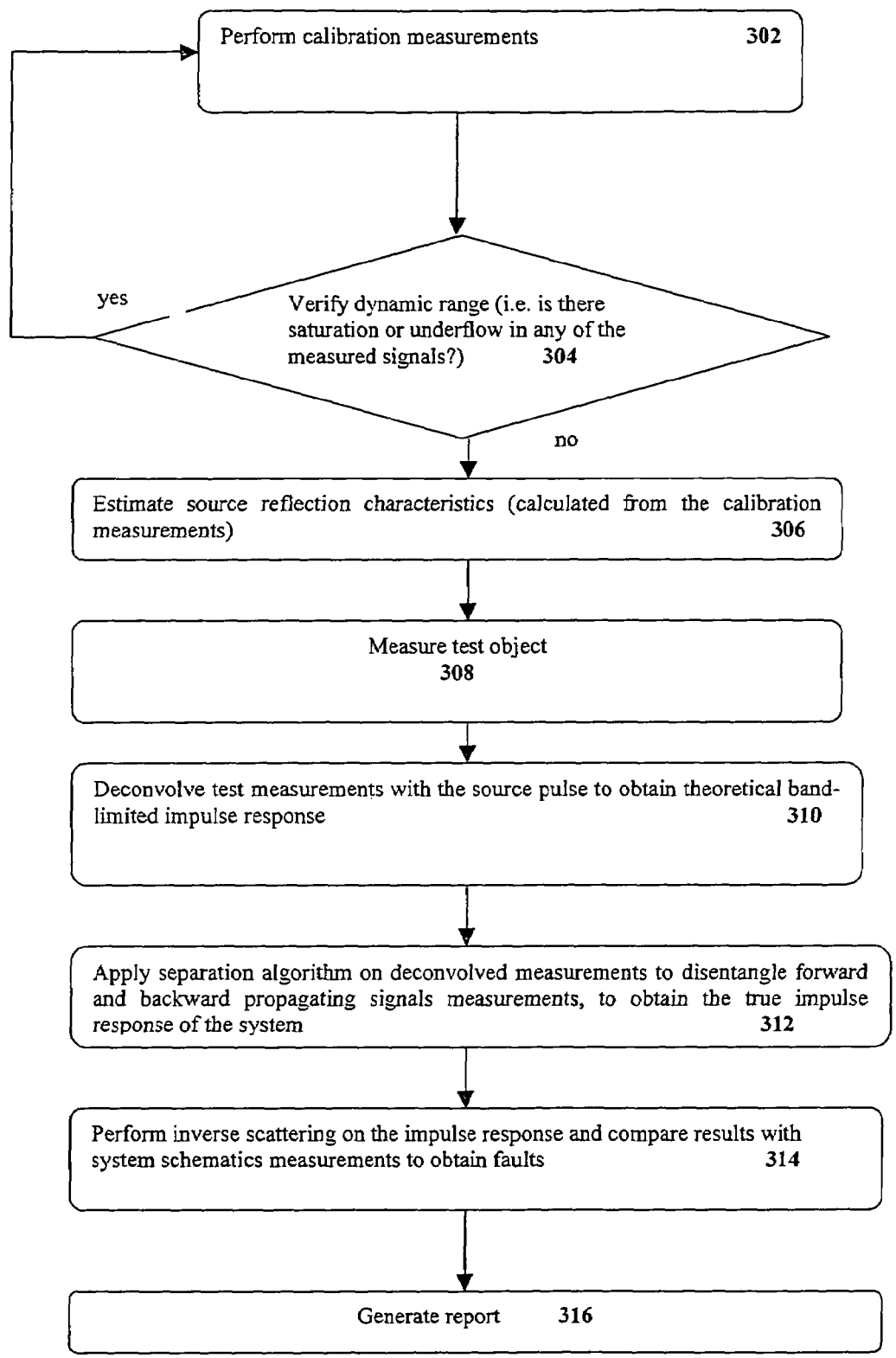
FIG. 3 shows a flow chart of the main steps in a method of use of the APR of FIG. 2.

FIG. 3 shows a flow chart of the main steps in a method of use of the APR of FIG. 2. A calibration to determine two parameters (described in more detail below) is carried out in step 302. A check to establish the dynamic range of the calibration measurements is performed in step 304. If there is either overflow or underflow, gains are adjusted manually (as described below) and step 302 is repeated. If there is no overflow or underflow the process continues to step 306, in which the source reflection characteristics (calculated from the calibration measurements and used later in the separation algorithm) are determined. The test object is measured, and alignment with calibration measurements to obtain time alignment is performed in step 308. In step 310 the test measurements are deconvolved with the source pulse, which is the pulse transmitted by the transmitter, obtained in the calibration phase. This gives the theoretical band-limited impulse response. At this stage, there is still an overlap of forward and backward propagating signals. The separation algorithm is applied to disentangle forward and backward propagating signals measurements in order to obtain the true impulse response of the system in step 312. An inverse scattering procedure is applied to the impulse response, and compared to the system schematics to obtain the searched-for faults, in step 314. Finally, a report is generated in step 316, exemplarily on a graphic user interface (GUI). The following provides more details of each step in the method.

Calibration: Steps 302, 304 and 306

The calibration has three main purposes: a) to measure the exact form of the acoustic excitation pulse $P_1$ emanating from transmitter 210; b) to find the exact form of the impulse response $H_i$ of the loudspeaker (source) and c) to verify that the hardware and software are correctly adjusted to utilize the full available dynamic range, without causing undue saturation at any stage. Calibration thus involves the following:

a. Finding $P_1$: A first measurement is carried out towards finding $P_1$. This requires performing a measurement in which no reflections arrive from the object or its termination till the excitation pulse dies out. This can be accomplished by several means:

(i) with a semi-infinite tube (practically, for the system of the present invention, at least 1.8 meter long) attached to APR system 200 as an "object". That is, the semi-infinite tube is "object" 214 shown in FIG. 2 in this part of the general measurement. Its length is such that the excitation pulse dies out before reflections arrive at sensor 208 from the end of the tube (which can be open or plugged, as this has no practical effect). This tube can be coiled to make it more portable. When tube 214 is attached, no reflections are created at the connection (joint) between it and mixed wave tube 212. Therefore, there is no overlap of left and right propagating waves at sensor 208 during the entire length of the excitation pulse.

(ii). In some cases, the object of interest has no faults. Thus, no reflections arrive at the microphone until $P_1$ dies out. In this case, $P_1$ can be extracted from measurements of the object itself, in step 308 below.

b. Finding $H_i$. This can be done using two different procedures: (i) carrying out a measurement with a rigid plug attached to APR system 200 as an "object", giving a signal termed $P_M^p$, where the superscript 'p' denotes the fact that the object is the rigid plug. $H_i$ is extracted directly from $P_M^p$ by a theoretical calculation (see below), or (ii) measuring $P_M^p$ as in (i) and performing an additional measurement instead of the theoretical calculation of $H_s$. These two alternatives are explained now in more detail.

(i) The plug presents a perfectly rigid termination, so that the impulse response $H_s$ of the length of the right half of the tube from microphone 208 to the plug (which we mark as L) can be modeled theoretically [Amir et al., "Losses in tubular acoustic systems", Acustica 82, pp. 1-8 (1996)]. Thus, equation (1) above can be applied where $H_i$ is now unknown, $H_s$ is taken from the theoretical calculation [Amir et al., "Losses in tubular acoustic systems", Acustica 82, pp. 1-8 (1996)] and $Z_i = P_M^p/P_1$. The theoretical calculation for $H_s$ can still present problems in accuracy. When necessary, increased accuracy in calculating $H_s$ can be attained as follows: inaccuracies in the theoretical calculation of $H_s$ will result in spurious peaks showing up in the calculated $H_i$. Using a rational approximation for $H_i$, the parameters of the approximation can be optimized using a Mean Square Error (MSE) criterion to minimize these spurious peaks.

(ii) To avoid the theoretical calculation of $H_s$ altogether, an additional measurement is carried out on an object having the exact same length L as the distance between sensor 208 and the end of mixed tube 212. We term this measurement $P_M^{p2}$. When this object is attached and plugged, the distance from sensor 208 to the plug (plugged object end) is now 2 L, having an impulse response $H_s^2$. We can now apply equation (1) twice: once when using $Z_i = P_M^p/P_1$, which provides $H_s$, and the second time when using $Z_i = P_M^{p2}/P_1$, which provides $H_s^2$. This gives two equations with two unknowns $H_s$ and $H_i$. That is $$H_s = \frac{\frac{P_M^o}{P_1} - 1}{\frac{P_M^o}{P_1} \cdot H_i - 1} \cdot \frac{P_1}{P_1} = \frac{P_M^o - P_1}{P_M^o \cdot H_i - P_1} \quad (2a)$$

$$H_s^2 = \frac{\frac{P_M^{p2}}{P_1} - 1}{\frac{P_M^{p2}}{P_1} \cdot H_i - 1} \cdot \frac{P_1}{P_1} = \frac{P_M^{p2} - P_1}{P_M^{p2} \cdot H_i - P_1} \quad (2b)$$

Figure 4:
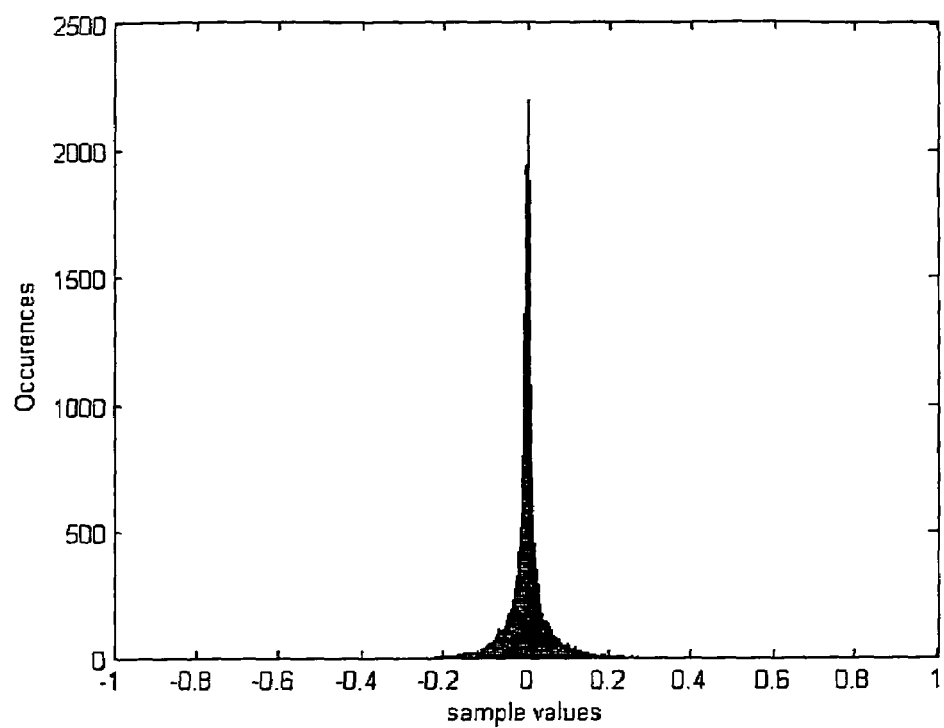
FIG. 4 shows the distribution of sample values in a signal with no saturation.
Figure 5:
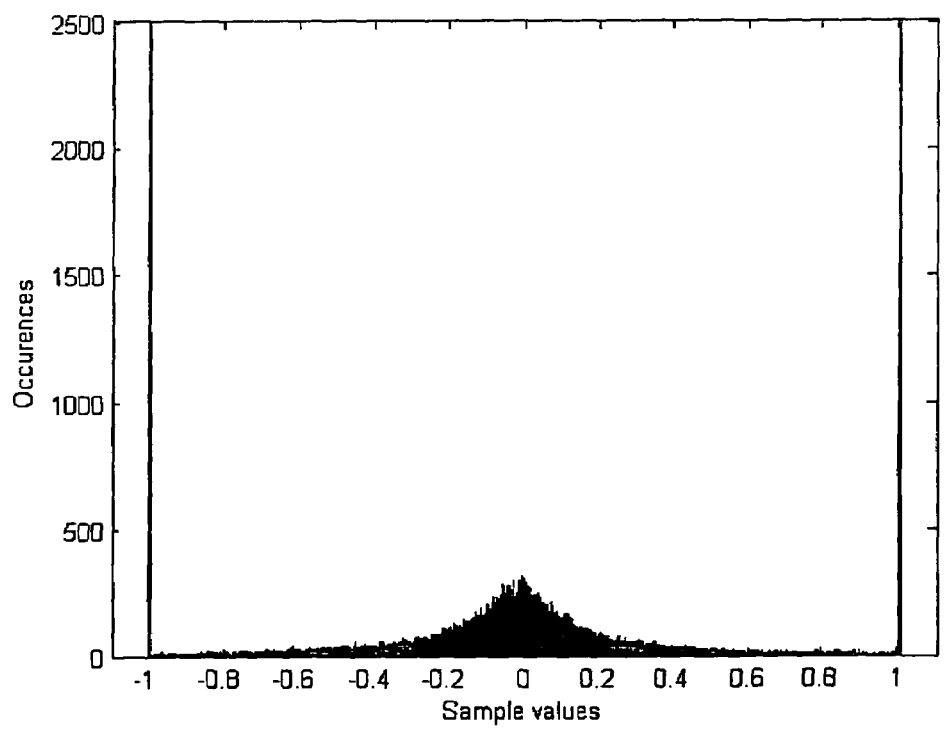
FIG. 5 shows the distribution of sample values in a signal with saturation at the input to the data acquisition board.
Figure 6:
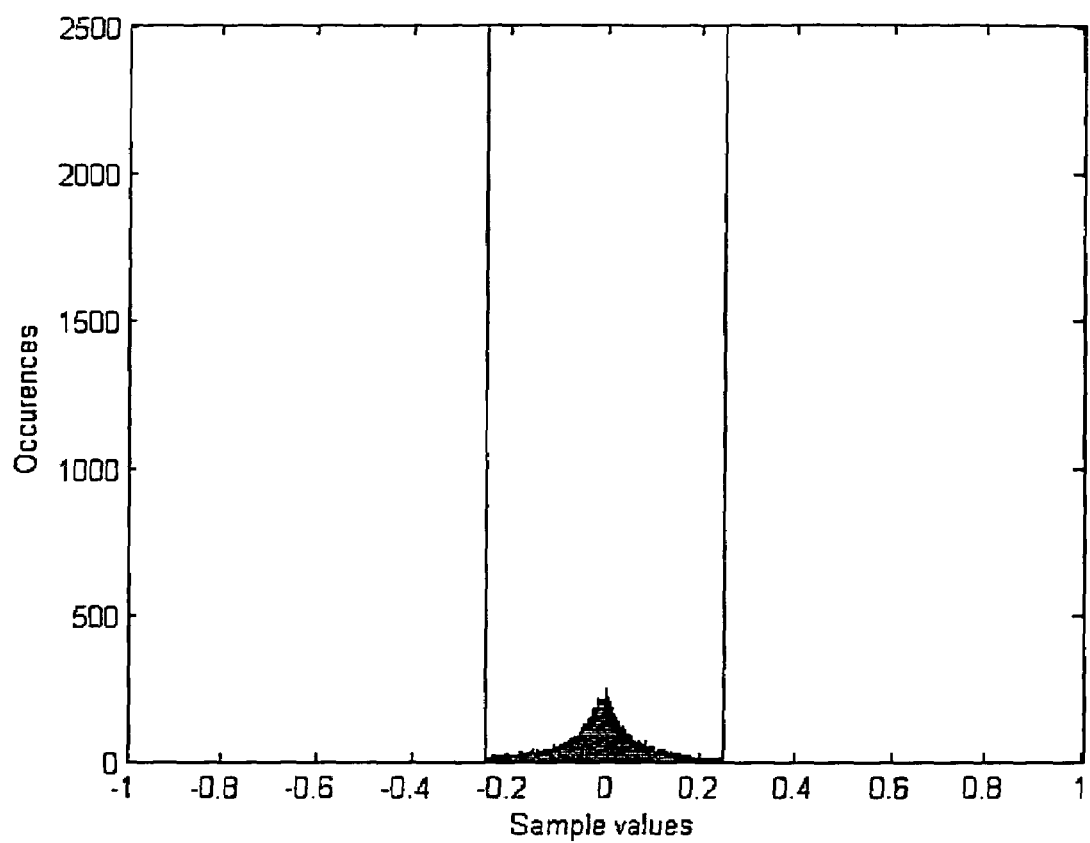
FIG. 6 shows the distribution of sample values in a signal with saturation in an analog component.

$H_s$ is now not required explicitly, and it is sufficient to solve for $H_i$.

c. When carrying out both stages (i) and (ii), the amplitudes of the emitted/received signals are controlled by separate gain adjustments at several different points: in the digital signal synthesized in the computer, in the amplifier driving the transmitter, in the preamplifier, and in the DAQ. Incorrect adjustment of any of these can cause one of two problems: underutilization of the dynamic range, reducing the effective number of bits in the recorded signals; or saturation, creating large nonlinear distortions in the form of clipping. Correct utilization of dynamic range is verified by two novel means:

(i) The voltage levels of sample values in the raw recorded signal coming from the DAQ are histogrammed. A signal with no saturation will give a distribution that is nearly normal and clearly symmetrical, as shown in FIG. 4. Saturation of the DAQ will give abnormally large values in the histogram at −1 and 1, as in FIG. 5. This means that the input gain to the DAQ must be readjusted. Saturation in one of the amplifiers or preamplifiers will give abnormally high values in the histogram at values less than 1 and more than −1, as shown in FIG. 6. This means that the user must readjust gains manually, and the measurements must be repeated to verify that saturation has been eliminated.

(ii) The number of effective bits used by the raw signal is indicated by the number of discrete voltage values in the raw signal, which we denote N. The base-2 logarithm of N is the number of effective bits. Thus, when saturation is eliminated as outlined in the previous step, $\log_2(N)$ is calculated. The result should be approximately 15, since if it is higher, saturation is uncomfortably close, and if it is lower, the dynamic range is underutilized. As in the previous step, gains are adjusted and repeated measurements carried out until this is the case.

Visual indications of (a) and (b) above are presented to the user during the calibration process, to ensure all gains are thus correctly adjusted.

We emphasize that the calibration procedure described above can inventively be applied to any APR system. Therefore, the calibrations steps of measuring $P_1$ and using the measured $P_1$ to determine $H_i$ form, by themselves, an inventive calibration method of APR systems.

Object Measurement: Step 308

After the calibration process, object 214 to be examined is attached to tube 212 (replacing the plug) and a measurement is obtained. This measurement gives a signal termed $P_M^o$, where the superscript "o" denotes "object".

Measurement Analysis and Interpretation: Steps 310-316

Three alternative methods are proposed here to analyze measurement $P_M^o$, depending on prior knowledge of the system being tested and the objectives of the test.

d. Unknown geometry: Measurements are carried out using the short tubes, resulting in overlapping acoustic waves. Using the information from the calibration measurements, the impulse response of the object is mathematically separated from the overlapping measurement, using a unique derivative of equation (1) above:

$$H_s = \frac{\frac{P_M^o}{P_1} - 1}{\frac{P_M^o}{P_1} \cdot H_i - 1} \cdot \frac{P_1}{P_1} = \frac{P_M^o - P_1}{P_M^o \cdot H_i - P_1} \quad (3)$$

In this equation $Z_i$ of equation (1) is replaced by $P_M^o/P_1$. $P_1$ is the excitation pulse, and the superscript "p" for "plugged" is replaced by "o" for "object". This equation is mathematically equivalent to (1) but more robust in practice, since it involves fewer divisions in the frequency domain, and is therefore more immune to accumulation of numerical errors, which is critical in this application. This ensures a much more accurate measurement than has been obtained in previous efforts described in the literature. This measurement is then input into a bore reconstruction algorithm, as described in the literature [Amir1], to find the internal geometry of the object, detecting leaks or blockages.

e. Known geometry: In cases where an object of an arbitrary known geometry composed of a variety of tubes, connections, junctions, etc., is being examined for defects, the simulated response of the object, $H_s$ is calculated theoretically [Amir1]. This calculated response is then compared with the measured response obtained from equation 3. Defects show up as discrepancies between these two, mainly in the form of sharp peaks (negative peaks indicate leaks, positive peaks indicate obstructions) in the impulse response. The major confounding factor in identifying these peaks correctly is the presence of noise. To facilitate the process of identifying these peaks correctly, we take advantage of the fact that leaks are liable to occur primarily in connectors. In the case of known geometry, the locations of all the connectors are known a-priori. Since there is a one to one correspondence between the temporal axis of the impulse response and location along the tubes, only the appropriate times in the impulse response are searched for negative peaks, which indicate leaks.

f. Leaks in the absence of connectors: In certain cases such as heat exchangers, leaks characteristically occur at arbitrary locations. Leaks cause reflections whose mathematical formulation has been described previously in the literature [Chilekawa]. The mathematical model for the reflection from a leak can be used to create a matched filter [J.Y. Stein, "Digital Signal Processing—a Computer Science Perspective", John Wiley and Sons, 2000]. The reflection from a leak is attenuated according to the distance from the source. Therefore an adaptive matched filter is applied, with an impulse response that is attenuated as it is convolved with further and further reflections. The output of the matched filter is a function with sharp positive peaks at the location of leaks in the tube.

Pressurized System

A pressurized system is similar in operation to the gas-filled ambient-pressure system, though it is used for finding faults in pressurized gas filled pipe systems. This is due to the fact that some leaks (at O-rings or gaskets, for example) appear only under pressure. In this application the transducers are specially designed to operate under pressure, but are preferably off-the-shelf components. The plug (used in calibration, see below) and the connectors used for attaching an object require means for pressurizing the system.

Figure 7:
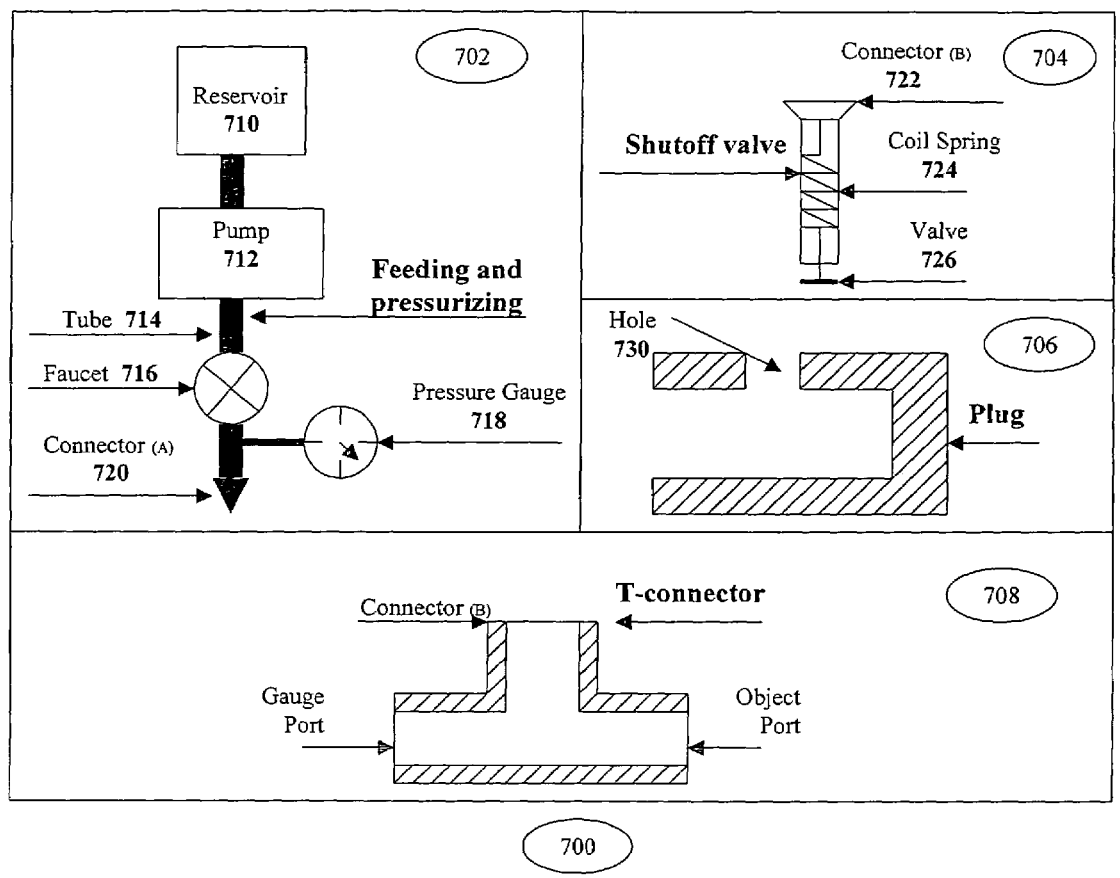
FIG. 7 shows schematically a preferred embodiment of subassemblies unique to calibrating and measuring a pressurized APR system.

A pressurized system uses the same components as in FIG. 2, and components of an additional "pressure assembly" 700, shown in FIG. 7. Note that pressurizing systems, their components and methods to assemble these components are well known in the art. The components described hereinbelow to provide the feature of "pressure" or "liquid-filling" to an APR system of the present invention are only exemplary, and other ways to implement pressurization and liquid filling may be used to achieve the same ends. They are also referred to as means for pressurizing of filling with liquid the mixed wave tube, calibration and test objects.

The components of a system 700 typically include a feeding and pressurizing subsystem 702, a shutoff valve 704 and a plug 706 or T-connector tube 708. Feeding and pressurizing subsystem 702 is operative to fill the tube of the acoustic gauge with the gas that the measured system contains to a required operating (static) pressure. It includes a gas reservoir 710 coupled to a pump 712 that is further coupled through a tube 714 to a faucet 716, a pressure gauge 718 and a first connector 720. Shutoff valve 704 is a normally closed valve that opens because of the pressure gradient that appears in the system during the feeding and pressurizing process. It includes a second connector 722, a coil spring 724 and a valve 726. Plug 706 seals the acoustic measurement gauge so that the calibration process can take place and includes a threaded hole 730 where shutoff valve 704 can be attached. T-connector tube 708 includes an object port, a gauge port and an opening for coupling to shutoff valve 704.

Figure 8:
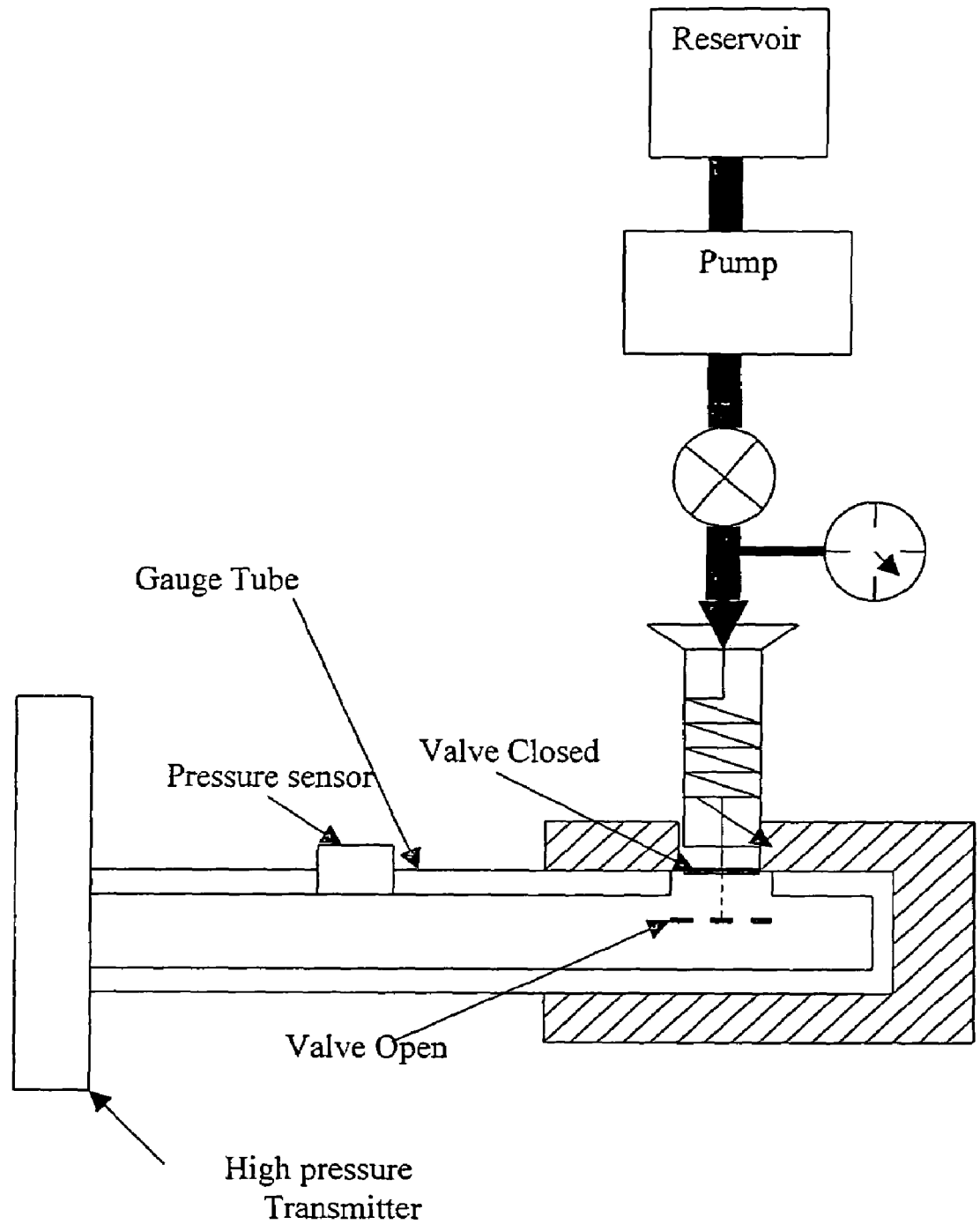
FIG. 8 shows schematically a preferred embodiment of a pressurized APR system when calibrating with a plug.
Figure 9B:
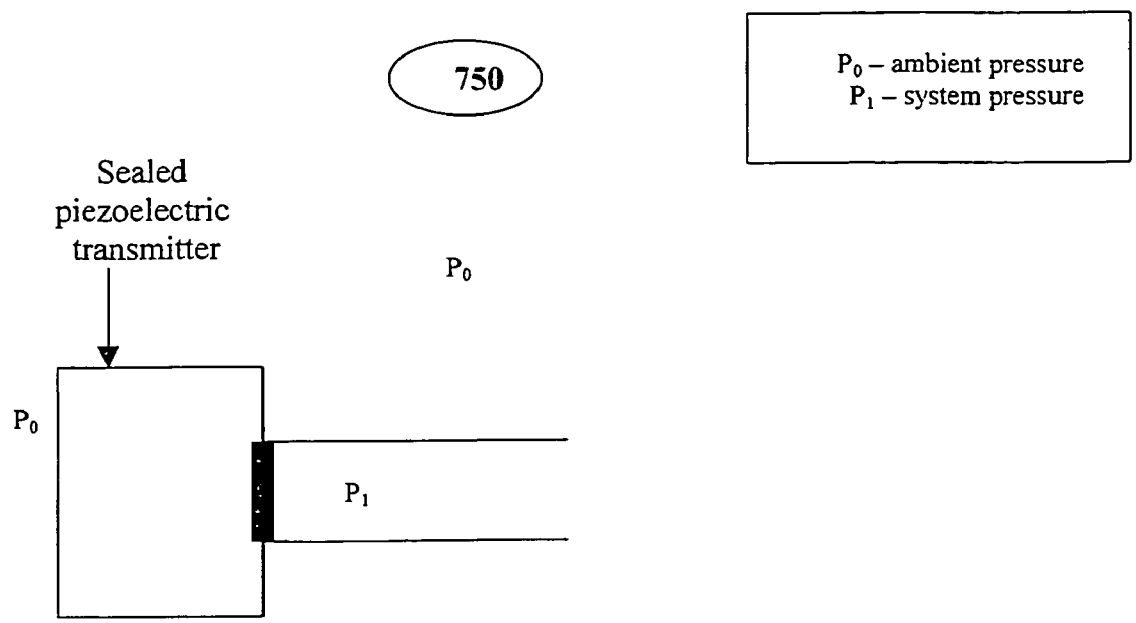

FIG. 8 shows the pressure assembly components assembled for a calibration procedure as an "object" attached to tube 212. Subsystems 702 and 704 are now connected via connectors 720 and 722. Shutoff valve 704 is permanently connected to plug 706. The calibration procedure includes steps of: filling the reservoir with the intended gas; feeding the gauge tube and pressurizing the gas to the requited pressure; closing the faucet, which leads to closing of the shutoff valve (since there is no pressure gradient between the pump and the inside of tube 212); and performing calibration measurements as described above for the un-pressurized system. Note that the transmitter used (732), shown in FIG. 9, operates under high pressure. In one embodiment, shown in FIG. 9a, transmitter 732 includes an off-the-shelf loudspeaker 736 encased in a pressurized casing 740. The volume enclosed by casing 740 and including loudspeaker 736 is at system pressure $P_1$. The casing ensures that system pressure $P_1$ is present on both sides of membrane 734. In another embodiment, the transmitter is shown in FIG. 9b, the transmitter may be an off-the-shelf piezoelectric transmitter 750, which is supplied in a sealed form, thus requiring no additional casing.

Figure 10:
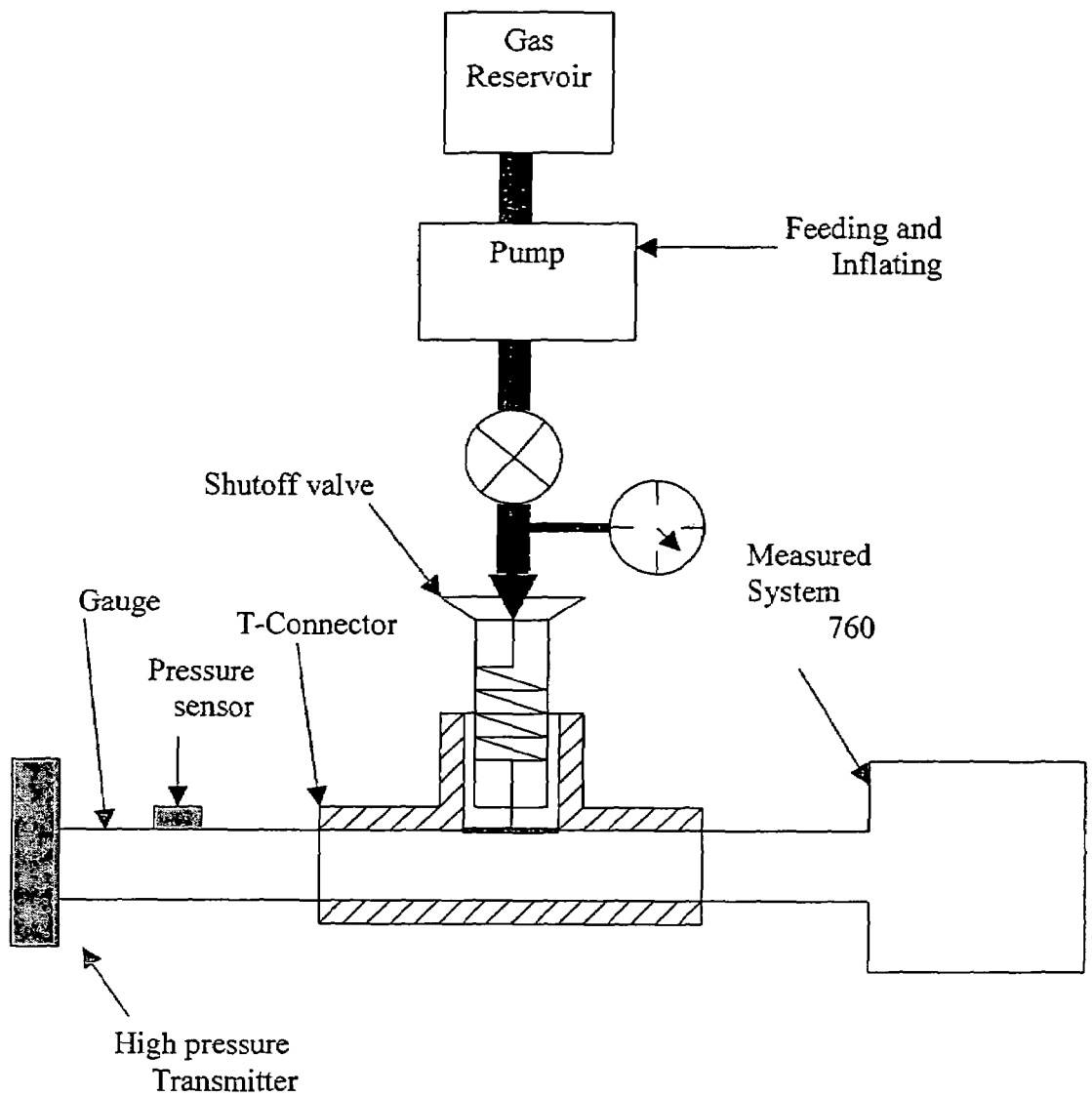
FIG. 10 shows schematically a preferred embodiment of a pressurized APR system when measuring an object.

In use for measuring a pressurized, gas filled object, plug 706 is replaced by T-connector tube 708, see FIG. 10. The figure shows a measured pressurized system (object) 760 attached through T-connector tube 708 to the rest of assembly 700. The pressurization and measurement sequence follows that described with reference to the calibrations above.

Liquid-Filled System

Figure 11:
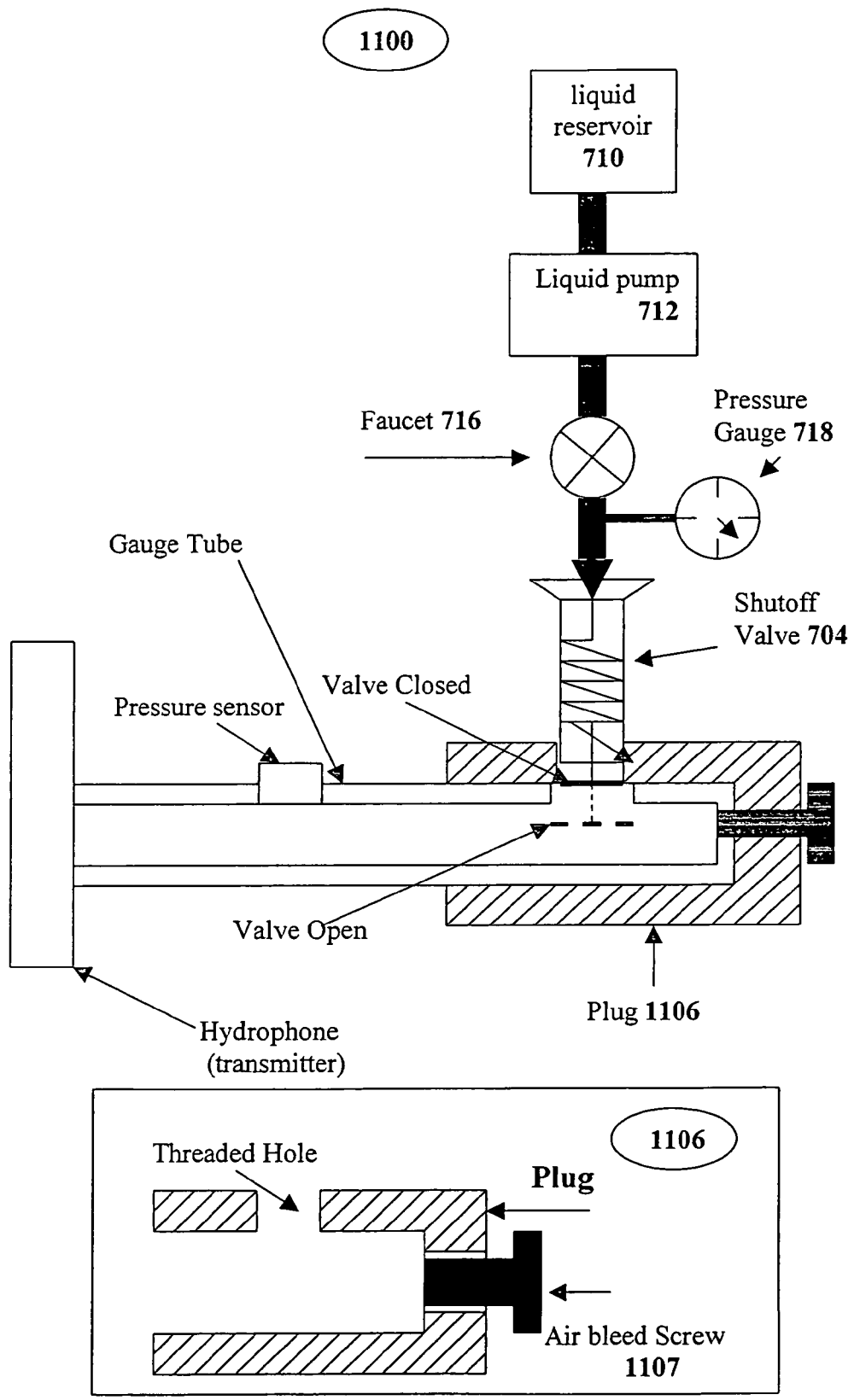
FIG. 11 shows schematically a preferred embodiment of a liquid filled pressurized/un-pressurized APR system when calibrating with a plug, along with the plug subassembly for liquid filled systems.
Figure 12:
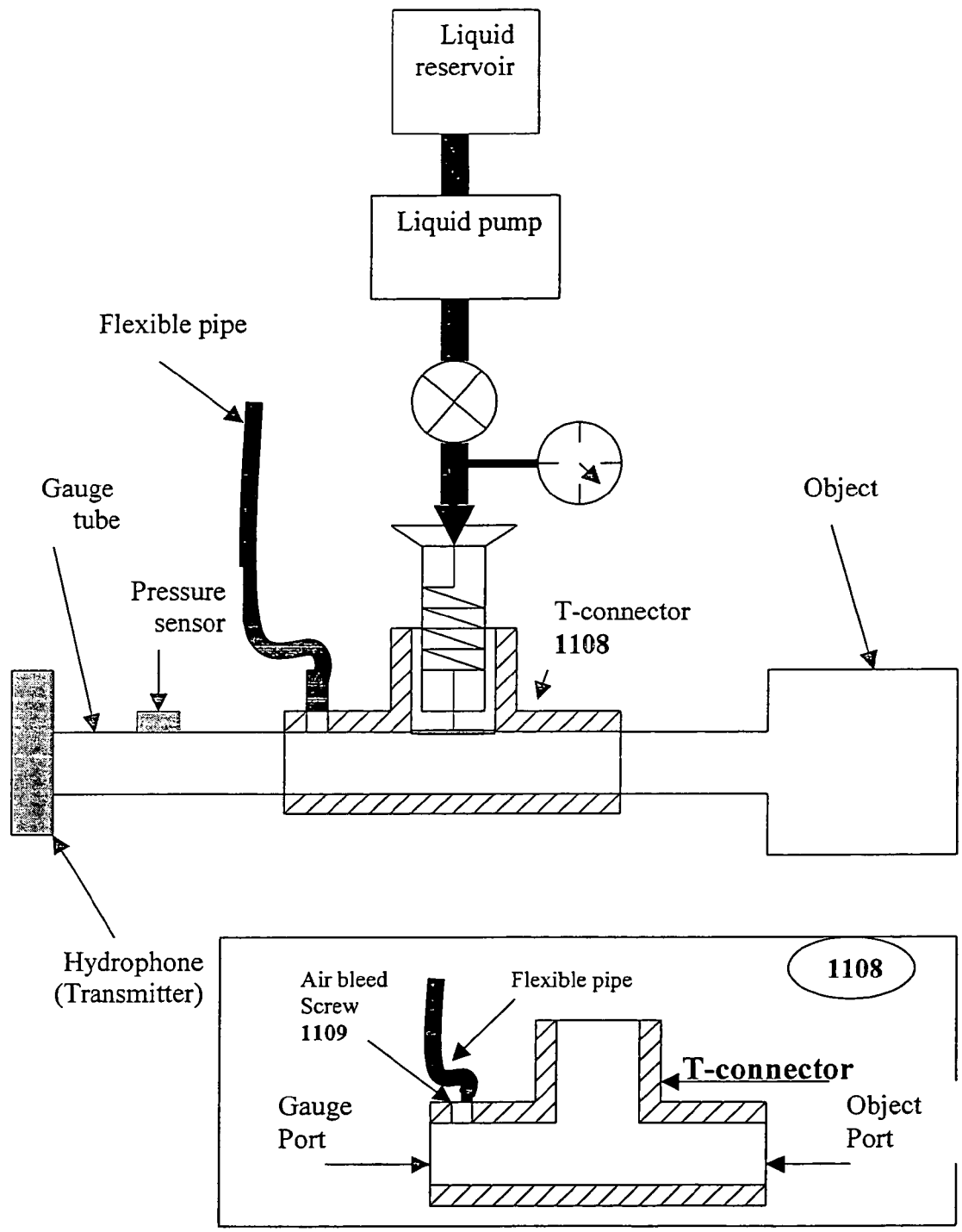
FIG. 12 shows schematically a preferred embodiment of a liquid filled pressurized/un-pressurized APR system when measuring an object, along with the T-connector subassembly for attaching a liquid filled object.

A liquid filled system is similar in operation to the gas filled system. It is used for finding faults in liquid filled pipe systems, either pressurized or at ambient pressure and requires several modifications beyond the ambient pressure gas filled system: the transducers are specially designed for operating in liquids, though they are off the shelf components. the plug (used in calibration) and the connectors used for attaching an object require means for filling the system with liquid and bleeding out any air trapped in the tubes. FIG. 11 shows a liquid filled test system used for calibrations, and FIG. 12 shows the same system used for measurement of an object A liquid filled system uses the same components as in FIG. 2, and components of an additional "pressure assembly", for example the assembly 1100, shown in FIGS. 11 and 12. Note that the components of assembly 1100 are essentially similar to those of assembly 700, except that the components are fit to handle pressurized or un-pressurized liquids instead of a pressurized gas. Exemplarily, a plug 1106 (similar to plug 706) now includes an air bleed screw 1107 for bleeding air out of the plug when filling with liquid, and a T-connector tube 1108 (similar to tube 708) now includes an air-bleed screw 1109, also for bleeding out the air when filling the system with liquid. The calibration and object measurements are carried out using essentially the same steps as for the gas pressurized system above.

The invention has now been described with reference to specific embodiments. Other embodiments will be apparent to those of ordinary skill in the art. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A method for non-destructive testing of an object, comprising steps of:
   a. providing an acoustic pulse reflectometry (APR) system having a wideband transmitter, a pressure sensor and a mixed wave tube with length 2 L;
   b. performing a calibration to obtain two calibration parameters, an exact acoustic excitation pulse form $P_1$ and a loudspeaker acoustic impulse response $H_i$;
   c. attaching the object to the APR system and performing a measurement to obtain an object test result $P_M^o$; and
   d. using $R_1$, $H_i$ and $P_M^o$ to obtain an object impulse response $H_s$;
   whereby the object impulse response reflects a status of the object.

2. The method of claim 1, wherein the obtaining of $P_1$ includes performing a measurement selected from the group consisting of a measurement that measures $P_1$ while a semi-infinite tube serves as the object and a measurement on an object in which any faults are far enough from the connection to the mixed wave tube so that $P_1$ can be extracted from this measurement.

3. The method of claim 2, wherein the obtaining of $H_i$ includes:
  i. replacing the object with a rigid plug,
  ii. carrying out a measurement with the rigid plug to obtain a value $P_M^p$, and
  iii. extracting $H_i$ directly from $P_M^p$ by a theoretical calculation that also uses the measured $P_1$.

4. The method of claim 3, wherein the extracting of $H_i$ directly from $P_M^p$ by a theoretical calculation includes calculating $H_i$ using the formula $$H_s = \frac{\frac{P_M^p}{P_1} - 1}{\frac{P_M^p}{P_1} \cdot H_i - 1} \cdot \frac{P_1}{P_1} = \frac{P_M^p - P_1}{P_M^p \cdot H_i - P_1}.$$

5. The method of claim 2, wherein the obtaining of $H_i$ includes:
  i. replacing the object with a rigid plug,
  ii. carrying out a first measurement $P_M^p$ with the rigid plug, and
  iii. replacing the plug with a second object with a length L, the second object having a distal plugged end, carrying out a second measurement to obtain an added measurement $P_M^{p2}$ and calculating $H_i$ using $P_M^p$, $P_M^{p2}$ and $P_1$.

6. The method of claim 5, wherein the calculating of $H_i$ using $P_M^p$, $P_M^{p2}$ and $P_1$ includes using the formulas:

$$H_s = \frac{\frac{P_M^p}{P_1} - 1}{\frac{P_M^p}{P_1} \cdot H_i - 1} \cdot \frac{P_1}{P_1} = \frac{P_M^p - P_1}{P_M^p \cdot H_i - P_1}$$

$$H_s^2 = \frac{\frac{P_M^{p2}}{P_1} - 1}{\frac{P_M^{p2}}{P_1} \cdot H_i - 1} \cdot \frac{P_1}{P_1} = \frac{P_M^{p2} - P_1}{P_M^{p2} \cdot H_i - P_1}$$

wherein $H_s^2$ is the acoustic response of the second object.

7. The method of claim 1, wherein the APR system further includes a data acquisition card (DAQ), a pre-amplifier and an amplifier, and wherein the step of performing the measurement on the object is preceded by a check to determine overflow/underflow conditions of the APR system, and, if overflow or underflow conditions are found, by adjusting gains of the DAQ, the pre-amplifier and the amplifier.

8. The method of claim 1, wherein the using of $P_1$, $H_i$ and $P_M^o$ to obtain an object impulse response $H_s$ includes applying a separation algorithm to disentangle forward and backward propagating signals in order to obtain the true impulse response of the object.

9. The method of claim 8, wherein the applying a separation algorithm includes using an equation $$H_s = \frac{\frac{P_M^o}{P_1} - 1}{\frac{P_M^o}{P_1} \cdot H_i - 1} \cdot \frac{P_1}{P_1} = \frac{P_M^o - P_1}{P_M^o \cdot H_i - P_1}.$$

10. The method of claim 1, wherein the object is selected from the group consisting of a pressurized object and a liquid filled object.

11. An acoustic pulse reflectometry (APR) system for non-destructive testing of a pressurized test object, comprising:
  a. a wide band signal transmitter for providing source acoustic pulses;
  b. a mixed wave tube for serving as conduit for the source pulses between the transmitter and object;
  c. a pressure sensor equidistantly spaced between two opposite ends of the mixed wave tube and used for sensing impulse responses from the test and calibration objects; and
  d. means for pressurizing the mixed wave tube, calibration and test objects, thereby enabling non-destructive testing of a pressurized object.

12. The system of claim 11, wherein the means for pressurizing include means for introduction and removal of a substance selected from the group consisting of a pressurized gas and a pressurized liquid.

13. The system of claim 12, wherein the pressurized liquid includes a liquid at atmospheric pressure.

14. An acoustic pulse reflectometry (APR) system for non-destructive testing of a test object filled with liquid, comprising:
  a. a wide band signal transmitter for providing source acoustic pulses;
  b. a mixed wave tube for serving as conduit for the source pulses between the transmitter and object;
  c. a pressure sensor equidistantly spaced between two opposite ends of the mixed wave tube and used for sensing impulse responses from the test and calibration objects; and
  d. means for introducing and removing a liquid into or from the mixed wave tube, calibration and test objects, thereby enabling non-destructive testing of a liquid filled object.

15. A method for calibrating an acoustic pulse reflectometry system that can be used to non-destructively measure an object, the method comprising steps of:
  a. measuring the acoustic excitation pulse form $f_1$ as emitted by the loudspeaker, and;
  b. using the measured $P_1$ to determine a loudspeaker acoustic impulse response $H_i$,
  whereby both $P_1$ and $H_i$ can be further used in determining non-destructively a status of a measured object.

16. The method of claim 15, wherein the step of measuring $P_1$ includes performing a measurement selected from the group consisting of a measurement that measures $P_1$ while a semi-infinite tube serves as the object and a measurement on an object in which any faults are far enough from a mixed tube so that $P_1$ can be extracted from the measurement.

17. The method of claim 16, wherein the using the measured $P_1$ to obtain $H_i$ includes:
  i. replacing the semi-infinite tube with a rigid plug,
  ii. carrying out a measurement with the rigid plug to obtain a value $P_M^p$, and
  iii. extracting $H_i$ directly from $P_M^p$ by a theoretical calculation that also uses the measured $P_1$.

18. The method of claim 16, wherein the using the measured $P_1$ to obtain $H_i$ includes:
  i. replacing the semi-infinite tube with a rigid plug,
  ii. carrying out a first measurement $P_M^p$ with the rigid plug, and
  iii. replacing the plug with a second object with a length L, the second object having a distal plugged end, carrying out a second measurement to obtain an added measurement $P_M^{p2}$ and calculating $H_i$ using $P_M^p$, $P_M^{p2}$ and $P_1$.

19. The method of claim 17, wherein the extracting of $H_i$ directly from $P_M^p$ by a theoretical calculation includes calculating $H_i$ using the formula $$H_s = \frac{\frac{P_M^p}{P_1} - 1}{\frac{P_M^p}{P_1} \cdot H_i - 1} \cdot \frac{P_1}{P_1} = \frac{P_M^p - P_1}{P_M^p \cdot H_i - P_1}.$$

20. The method of claim 18, wherein the calculating of $H_i$ using $P_M^p$, $P_M^{p2}$ and $P_1$ includes using the formulas:

$$H_s = \frac{\frac{P_M^p}{P_1} - 1}{\frac{P_M^p}{P_1} \cdot H_i - 1} \cdot \frac{P_1}{P_1} = \frac{P_M^p - P_1}{P_M^p \cdot H_i - P_1}$$

$$H_s^2 = \frac{\frac{P_M^{p2}}{P_1} - 1}{\frac{P_M^{p2}}{P_1} \cdot H_i - 1} \cdot \frac{P_1}{P_1} = \frac{P_M^{p2} - P_1}{P_M^{p2} \cdot H_i - P_1}$$

wherein $H_s^2$ is the acoustic response of the second object.

* * * * *

UNITED STATES PATENT AND TRADEMARK OFFICE
CERTIFICATE OF CORRECTION

PATENT NO. : 7,677,103 B2 Page 1 of 1
APPLICATION NO. : 11/495642
DATED : March 16, 2010
INVENTOR(S) : Amir et al.

It is certified that error appears in the above-identified patent and that said Letters Patent is hereby corrected as shown below:

Front Page

(73) Assignee should be corrected as follows:
change
"Acousticeve Ltd."
to
"Acousticeye Ltd."

Claim 1, column 12 line 60 should be corrected as follows:
change
"d. using $R_1$, $H_i$ and $P_M^o$ to obtain an object impulse…"
to
"d. using $P_1$, $H_i$ and $P_M^o$ to obtain an object impulse…"

Claim 15, column 14 line 41 should be corrected as follows:
change
"a. measuring the acoustic excitation pulse form $f_1$,…"
to
"a. measuring the acoustic excitation pulse form $P_1$,…"

Signed and Sealed this

Eighteenth Day of May, 2010

David J. Kappos
*Director of the United States Patent and Trademark Office*